United States Patent
Vettorello

(10) Patent No.: US 8,517,950 B2
(45) Date of Patent: Aug. 27, 2013

(54) PROCESS AND A DEVICE FOR DETERMINING CONDITIONS OF HYPOVOLEMIA

(76) Inventor: Marco Vettorello, Milan (IT)

( * ) Notice: Subject to any disclaimer, the term of this patent is extended or adjusted under 35 U.S.C. 154(b) by 0 days.

(21) Appl. No.: 13/222,692

(22) Filed: Aug. 31, 2011

(65) Prior Publication Data

US 2012/0053438 A1  Mar. 1, 2012

(30) Foreign Application Priority Data

Aug. 31, 2010  (IT) .............................. MI2010A1587

(51) Int. Cl.
  *A61B 5/02*  (2006.01)
  *A61B 5/04*  (2006.01)

(52) U.S. Cl.
  USPC ............ 600/482; 600/509; 600/371; 600/485

(58) Field of Classification Search
  None
  See application file for complete search history.

(56) References Cited

U.S. PATENT DOCUMENTS

| 6,027,453 A | 2/2000 | Miwa et al. |
|---|---|---|
| 2006/0178585 A1 | 8/2006 | Sharrock |
| 2010/0191128 A1 | 7/2010 | Shelley et al. |
| 2010/0256507 A1 | 10/2010 | Sharrock |
| 2011/0060531 A1 | 3/2011 | Sugo et al. |

FOREIGN PATENT DOCUMENTS

| EP | 0956817 A1 | 11/1999 |
|---|---|---|
| WO | 2010045556 A2 | 4/2010 |

OTHER PUBLICATIONS

Abstract, The American Surgeon, 2010, vol. 76, Issue 3, pp. 296-301 (Abstract),<www.ncbi.nlm.nih.gov>.
Search Report for Italian Application No. MI20101587 dated May 13, 2011.
Middleton, Paul M. et al., "Changes in left ventricular ejection time and pulse transit time derived from finger photoplethysmogram and electrocardiogram during moderate haemorrhage", Clin Physiol Funct Imaging, vol. 29, (2009), pp. 163-169.
Cooke, William H. et al., "Autonomic compensation to simulated hemorrhage monitored with heart period variability", Crit Care Med, vol. 36, No. 6, (2008), pp. 1892-1899.
Esch, Ben T. A. et al., "Construction of a lower body negative pressure chamber", Adv Physiol Educ, vol. 31, (2007), pp. 76-81.
Opreanu, Razvan C. et al., "Hematocrit, Systolic Blood Pressure and Heart Rate Are Not Accurate Predictors for Surgery to Control Hemorrhage in Injured Patients", The American Surgeon, vol. 76, (Mar. 2010), pp. 296-301 plus copyright page.

*Primary Examiner* — Brian T Gedeon
*Assistant Examiner* — Ankit Tejani
(74) *Attorney, Agent, or Firm* — Pearne & Gordon LLP

(57) ABSTRACT

An apparatus for determining an indicator parameter relating to a subject comprising at least an input line for receiving electrical signals coming from a electrodes, receiving a signal coming from a peripheral sensor predisposed to operate in a predetermined peripheral section of the subject's body; a control unit connected to the input line and configured for determining a value of an indicator value (iHAT) as a function of the instant of generation ($TG_j$) of a pressoric wave in relation to the heartbeat.

25 Claims, 8 Drawing Sheets

Results

| PRESSURE (MMHG) | SUBJ. NUMBERS | SBP (MMHG) | DBP (MMHG) | HR (BEATS/MIN) | IHAT (%) |
|---|---|---|---|---|---|
| 0 | 9 | 118±7 | 71±5 | 71±10 | 37.2±3.1 |
| -15 | 9 | 114±6 | 71±5 | 73±10 | 38.5±3.2* |
| -30 | 9 | 113±7 | 68±8 | 81±11* | 42.5±4.6** |
| -45 | 7 | 110±9 | 66±11 | 93±18** | 48.3±8.1 |
| -60 | 4 | 113±10 | 68±8 | 94±12* | 49.6±5.0** |
| -70 | 2 | 116±0 | 75±2 | 109±3 | 55.1±2.8 |
| -80 | 2 | 110±0* | 68 | 117±7 | 60.5±1.1 |

Fig. 10

PROCESS AND A DEVICE FOR DETERMINING CONDITIONS OF HYPOVOLEMIA

FIELD

A process and a device for determining conditions of hypovolemia in patients is described herein.

BACKGROUND

As is known, timely revealing of hypovolemia can be advantageous in numerous therapeutic or pre-therapeutic contexts.

In a non-limiting way, it is for example important to determine an eventual onset of internal haemorrhaging, in order to be able to intervene rapidly and in good time such as to prevent damage which can, in the worst cases, even lead to decease of a patient.

Identifying hypovolemy conditions is however not easy to do. In particular, the early identification of haemorrhages, while avoiding using invasive systems internal of the human body, is particularly complex as the site where the haemorrhage occurs is not evident by inspection of external tissues of the patient.

In the past research has been made into the analysis of various parameters with the aim of arriving at a verification of haemorrhage conditions which do not require access to the inside of the human body.

In particular the publication "Changes in left ventricular ejection time and pulse transit time derived from finger photoplethysmogram and electrocardiogram during moderate haemorrhage"—Clin Physiol Funct Imaging (2009)-29, pages 163-169, authors Paul M. Middelton et al., discusses the analysis of various parameters with the aim of verifying the existence of relations between haemorrhages induced by donation on donor subjects and certain signals detected in the donor.

In particular, the above publication uses the signal produced by an echo-cardiograph as well as the signal produced by a pulse oximeter in order to determine parameters such as: the interval $RR_i$ between successive R wave peaks, the PTT, the pulse transit time, LVET corresponding to the interval between onset and end of ventricular ejection time, the $RR_i$ gradient, the PPT gradient, the LVET gradient.

Although the document in question discusses how the presence of a haemorrhage can influence these parameters, not correlation is established among the various parameters, nor is any indication given for the practical and efficient determination of haemorrhage conditions, or more in general conditions of hypovolemia.

SUMMARY

In this situation, an aim of the present disclosure is to provide a new procedure and a new device for practical and efficient determination of conditions of hypovolemia.

A further aim 1s to provide a new device and a new procedure which enable determination of conditions of hypovolemia in a non-invasive way. i.e. which do not require introduction of any device into the patient's body.

It is in particular an aim of the disclosure to enable non-invasive determination of states of hypovolemia both during monitoring of the patient and in a successive stage after acquiring the various parameters required for verification of the eventual condition of hypovolemia.

A further aim of the disclosure is to disclose a procedure and a device that are able to reveal onset of haemorrhage conditions rapidly and such as to be able to detect these conditions when the haemorrhage has not reached a state of propagation which is excessively dangerous for the patient.

A further aim of the disclosure is to determine conditions of hypovolemia not only caused by haemorrhages but also determined by other causes such as sweating, loss of liquids due to various pathologies, transcutaneous losses of liquids caused by burns, vaso-dilation having various causes, hypovolemia determined by spinal lesions.

A final aim of the disclosure is to make available a procedure and a device which are able to offer simple and constructive identification and which are easy to apply, in a case of hypovolemia.

One or more of the above aims are substantially attained by a process and a device according to one of the accompanying claims.

Aspects are described herein below.

In a first aspect, an apparatus is provided for determining conditions of hypovolemia in a subject comprising:

at least an input line for receiving one or more signals coming from one or more electrodes predisposed to detect cardiac activity (for example 3 or more electrodes connected to the input line can be used) and for receiving a signal coming from at least a peripheral sensor predisposed to operate in a predetermined peripheral zone of the subject's body; for example a first input line can be used for the signal from the electrodes and a distinct second input line for the signal coming from the peripheral sensor;

a control unit connected to the input line and configured to execute the steps of correlating the signal from the electrodes with the signal from the peripheral sensor and determining at least a value of an indicator parameter of hypovolemia which is a function of the correlation of the two signals.

In a second aspect in accordance with the first aspect, the correlation step comprises:

determining, from the signal or signals coming from the electrodes through the input line, an instant $TG_j$ in which a pressoric wave is generated in relation to a heartbeat, determining, from the signal coming from the peripheral sensor through the input line, an instant of peripheral propagation $TP_j$ in which the pressoric wave relating to the predetermined peripheral zone of the subject's body subjected to monitoring reaches the predetermined peripheral section, calculating at least a value of an indicator parameter as a function of at least the instant of generation $TG_j$ and the instant of peripheral propagation TP.

In a third aspect, in accordance with the second aspect, the unit is configured to determine a temporal interval $\Delta T_j$ between a heartbeat and a following heartbeat, and calculating the indicator value parameter value as a function of at least:

the instant of generation $TG_j$, the instant of peripheral propagation $TP_j$ and the temporal interval $\Delta T_j$.

In a fourth aspect, the temporal interval $\Delta T_j$ is determined by calculating the time interval between an instant of generation $TG_j$ and the successive instant of generation $TG_{j+1}$.

In a fifth aspect, in accordance with one or more of the preceding aspects, the control unit is configured to determine an ECG chart from the first signal and to identify the instant of generation $TG_j$ as the moment in which, in the ECG chart, a wave $R_j$ relating to a wave sequence $QRS_j$ exhibits a maximum peak.

In a sixth aspect in accordance with any one of the preceding aspects, the peripheral sensor is a pulse oximeter.

In a seventh aspect according to the preceding aspect, the control unit is configured to determine, from the signal originating from the pulse oximeter, a saturometer curve, and to identify the instant of propagation $TP_j$ by detecting a peak in amplitude of the saturometer curve.

In an eighth aspect, according to any preceding aspect, the value of the indicator parameter is calculated as function of a temporal delay $\delta T_j$ occurring between the instant of generation $TG_j$ and the instant of peripheral propagation $TP_j$.

In a ninth aspect according to the eighth aspect, the value of the indicator parameter is calculated as function of the temporal delay $\delta T_j$ divided by the time interval occurring between two successive heartbeats $\Delta T_j$.

In a tenth aspect, according to any one of the preceding aspects, the control unit is configured to cyclically repeat the calculation of the value of the indicator parameter a plurality of times.

In an eleventh aspect according to any one of aspects from the 7th to 10th, the control unit is configured to temporally synchronise the ECG chart and the saturometer curve. For example, the temporal synchronisation comprising relating values of the ECG chart and the saturometer curve (represented in the y-axis of a Cartesian axis system) to a same temporal axis (the x axis of the Cartesian graph), the relative values at a same temporal instant being represented on the ECG chart and on the saturometer curve at a same point on the x-axis.

In a twelfth aspect, according to any one of the preceding aspects, the apparatus is characterised in that it comprises at least a first filter active on the signal or signals for filtering the noise due to feeding.

In a thirteenth aspect, according to any preceding aspect, the apparatus is characterised in that it comprises at least a second filter active on the signal or signals for filtering the noise due to any existing tremor in the patient.

In a fourteenth aspect according to any one of the preceding aspects, the apparatus is characterised in that it comprises at least a third filter that is active on the signal or signals for filtering the noise due to breathing motions of the patient.

In a fifteenth aspect according to any one of the aspects from the fifth to the fourteenth, the signals are sampled at a respective frequency, optionally greater than or equal to 300 Hertz, for respectively determining the ECG chart and the saturometer.

In a sixteenth aspect according to any one of the preceding aspects, the control unit is configured to calculate indicator parameter a plurality of times in relation to a plurality of successive heartbeats.

In a seventeenth aspect according to any one of the preceding aspects, the control unit is configured to determine a mean value $iHAT_{med}$ of the indicator parameter, the mean value being calculated as a mean of a plurality of parameter values iHAT related to a plurality of successive heartbeats.

In an eighteenth aspect, according to any preceding aspect, the control unit is configured such as to compare the value of the indicator parameter with a respective threshold value M.

In a nineteenth aspect, according to any preceding aspect, the control unit is configured to compare the mean value of the indicator parameter with a respective threshold value.

In a twentieth aspect, according to the preceding aspect, the apparatus comprises a viewing device; the control unit is connected to the viewing device and is configured to control the viewing device in order to provide a signal when the instant value and/or the mean value of the indicator parameter exceeds the predetermined threshold value.

In a twenty-first aspect, according to the preceding aspect, the control unit is configured such as to form a plurality of viewing portions on the viewing device, distinct from one another.

In a twenty-second aspect according to the preceding aspect, the control unit is configured to visualise a graph on one of the viewing portions, which graph is temporally synchronized, of the ECG chart and the pulse oximeter signal.

In a twenty-third aspect according to the twenty-first or twenty-section aspect, the control unit is configured to visualise, on a viewing portion of the viewing device, a graphic representation of a progression of the time indicator parameter value.

In a twenty-fourth aspect, according to the twenty-first, twenty-second or twenty-third aspect, the control unit is configured to visualise, on a viewing portion of the viewing device, a graphic representation of a progression of the mean value of the time indicator parameter.

In a twenty-fifth aspect, according to any aspect from the twenty-first to the twenty-fourth, the control unit is configured to differentially represent respective fiduciary markers relative to the peaks $R_j$ of the wave R of the ECG charge and to the peaks $S_j$ in the saturometer curve.

In a twenty-sixth aspect according to any aspect from the twenty-first to the twenty-fifth, the control unit is configured to represent in a first graphic mode (for example in a first colour), the instant value and/or the mean value of the indicator parameter when lower than the threshold and in a second graphic mode (for example in a second colour, different from the first), the instant value and/or the mean value of the indicator parameter (iHAT; $iHAT_{med}$) when higher than the threshold M.

In a twenty-seventh aspect, according to any preceding aspect, the control unit is configured such as to compare the value of the indicator value and/or the mean value of the indicator parameter with a plurality of threshold values defining a series of potentially dangerous intervals, the control unit being configured to signal when each of the threshold values has been exceeded in a graphically different way.

For example, on exceeding each threshold, the control unit can represent in a graphically differentiated way the value of the indicator parameter such as to attract the user's attention should dangerous conditions of hypovolemia be present.

In a twenty-eighth aspect, according to any aspect from the eighteenth to the twenty-seventh, the threshold corresponds to a value of 58% or 0.58 according to whether the value of the indicator parameter is expressed respectively as a percentage or a decimal.

In a twenty-ninth aspect, according to any aspect from the eighteenth to the twenty-seventh, the threshold value, expressed as a percentage, is comprised, between 55% and 60%, optionally 58%; the control unit being optionally configured to enable programming of the threshold value.

In a thirtieth aspect, according to any preceding aspect, the threshold value, expressed as a percentage, is comprised between 55% and 60%.

In a thirty-first aspect, according to any preceding aspect, the control unit is configured to enable programming the threshold value.

In a thirty-second aspect, according to any preceding aspect, the control unit is programmed to:
receive the patient's age;
determine the threshold value or values according to the age of the subject.

In a thirty-third aspect, according to any preceding aspect, the control unit is configured such as to determine, at each heartbeat, first the peak R in the ECG chart, and then, should the calculation of the peak R allow to identify a value of R, the peak of the saturometer curve. In practice, in each cycle (i.e. at each heartbeat), the control unit determines the peak $S_j$ in the pulse oximeter curve following the peak $R_j$ in the ECG chart only if the identification of the $R_j$ has been successful.

In a thirty-fourth aspect, according to any one of the preceding aspects, a monitoring system comprises:
a plurality of electrodes destined to be engaged to a patient such as to detect electric signals determined by cardiac activity,
a peripheral sensor, for example a pulse oximeter, destined to be engage to a peripheral section (for example a finger or an earlobe) of a patient, and an apparatus as in one of the preceding claims.

In a thirty-fifth aspect according to the thirty-fourth aspect, the electrodes are connected to an input line of the apparatus, for example with a first input line, and the peripheral sensor with an apparatus line which can be the same line or a second line, distinct from the first line. Should the same input line be used for receiving both the signal from the electrodes and the signal from the peripheral sensor, the apparatus comprises a signal separator, for example integrated in the control unit, able to separate the signals relating to the electrodes from those coming from the peripheral sensor.

In a thirty-sixth aspect, a process is comprised for determining a parameter indicative of conditions of hypovolemia in a subject comprising the following steps:
positioning on the subject a plurality of electrodes (non-invasively for example on the thorax and/or the abdomen) such as to detect electric signals determined by cardiac activity,
positioning on the subject (non-invasively) at least a peripheral sensor in a predetermined peripheral section of the subject's body (for example on a finger or an ear),
receiving one or more signals coming from the electrodes and a signal coming from the peripheral sensor;
correlating the signal from the electrodes with the signal from the peripheral sensor, and determining at least a value of the indicator parameter as a function of the correlation of the two signals.

In a thirty-seventh aspect, according to the thirty-sixth aspect, the step of correlating comprises:
determining from the signal or signals coming from the electrodes, an instant $TG_j$ in which a pressoric wave is generated that relates to a heartbeat,
determining, from the signal coming from the peripheral sensor through the input line, an instant of peripheral propagation $TP_j$ in which the pressoric wave reaches the predetermined peripheral section of the body of the person subjected to monitoring,
calculating a value of the indicator parameter as a function of at least the instant of generation $TG_j$ and the instant of peripheral propagation $TP_j$.

In a thirty-eighth aspect according to the thirty-seventh aspect, the procedure comprises determining a temporal interval $\Delta T_j$ between a heartbeat and a following heartbeat, and calculating the indicator parameter value as a function of at least:
the instant of generation $TG_j$,
the instant of peripheral propagation $TP_j$ and
the temporal interval $\Delta T_j$.

In a thirty-ninth aspect, according to the thirty-eighth aspect, the time interval $\Delta T_j$ is determined by calculating the time interval between an instant of generation $TG_j$ and the successive instant of generation $TG_{j+1}$.

In a fortieth aspect, according to any one of the preceding aspects from the 36th to the 39th, the procedure comprises determining, from the signal coming from the electrodes, an ECG chart and identifying the instant of generation $TG_j$ as a moment in which, in the ECG chart, a wave $R_j$ relating to a sequence of waves $(QRS)_j$ exhibits a maximum peak.

In a forty-first aspect, according to any one of aspects from the thirty-sixth to the fortieth, the peripheral sensor is a pulse oximeter.

In a forty-second aspect, according to the preceding aspect, the procedure comprises determining from the signal of the pulse oximeter a saturometer curve and identifying the instant of peripheral propagation $(TP_j)$ by detecting a peak in amplitude of the saturometer curve.

In a forty-third aspect according to any aspect from the thirty-sixth to the forty-first, the value of the indicator parameter is calculated as a function of the time delay $\delta T_j$ occurring between the instant of generation $(TG_j)$ and the instant of peripheral propagation $(TP_j)$.

In a forty-fourth aspect, according to the forty-third aspect, the value of the indicator parameter is calculated as a function of the temporal delay $\delta T_j$ divided, by the time interval occurring between two successive heartbeats $\Delta T_j$.

In a forty-fifth aspect, according to any aspect from the thirty-sixth to the forty-fourth, the procedure comprises repeating the calculation of the value of the indicator parameter cyclically and a plurality of times.

In a forty-sixth aspect, according to any aspect from the thirty-sixth to the forty-fifth, the procedure comprises temporally synchronizing the first and the second signal. For example, the temporal synchronisation comprises referring values of the ECG chart and the saturometer curve (represented in the y-axis of a Cartesian axis system) to a same temporal ic axis (the x axis of the Cartesian graph), such that the relative vales at a same temporal instant are represented on the ECG chart and on the saturometer curve at a same point on the x-axis.

In a forty-seventh aspect, according to any aspect from the 36th to the 46th, the indicator parameter is calculated a plurality of times in relation to a plurality of successive heartbeats.

In a forty-eighth aspect, according to any aspect from the 36th to the 47th, the procedure comprises determining a mean value of the indicator parameter, calculated as a mean of a plurality of values of the parameter referred to a plurality of successive heartbeats.

In a forty-ninth aspect according to any aspect from the thirty-sixth to the forty-eighth, the procedure comprises comparing the value of the indicator parameter or the mean value thereof with a respective threshold value and generating a warning signal when the value or, respectively the mean value, as calculated is higher than the respective threshold.

In a fiftieth aspect, the procedure comprises representing, in a first graphic mode (for example in a first colour) the instant value and/or the mean value of the indicator parameter when lower than the threshold and in a second graphic mode, (for example in a second colour, different from the first), the instant value and/or the mean value of the indicator parameter when higher than the threshold.

In a fifty-first aspect, according to any aspect from the thirty-sixth to the fiftieth, the threshold corresponds to a value of 58% or 0.58 according to whether the value of the indicator parameter is expressed respectively as a percentage or a decimal.

In a fifty-second aspect according to any aspect from the thirty-sixth to the fifty-first, the threshold value, expressed as a percentage, is comprised between 55% and 60%, optionally 58%.

In a fifty-third aspect, according to any aspect from the thirty-sixth to the fifty-second, the procedure comprises:
receiving the patient's age;
determining the threshold value or values according to the age of the subject.

In a fifty-fourth aspect, according to any aspect from the thirty-sixth to the fifty-third, the procedure comprises determining, at each heartbeat, first the peak R in the ECG chart, and then, should the calculation of the peak R be correct, the peak of the saturometer curve. In practice, in each cycle at each heartbeat), the control unit determines the peak $S_j$ in the pulse meter curve following the peak $R_j$ in the ECG chart only if the identification of the $R_j$ has been successful.

A fifty-fifth aspect concerns an apparatus for determining conditions of hypovolemia in a subject, comprising:
at least an input line for:
  receiving one or more electrical signals coming from one or more electrodes predisposed to detect cardiac activity;
  receiving a signal coming from a peripheral sensor predisposed to operate in a predetermined peripheral section of the subject's body;
a control unit connected to the input line and configured for:
  determining, from the signal or signals coming from the electrodes through the line, an instant $TG_j$ in which a pressoric wave is generated in relation to a heartbeat,
  determining, from the signal coming from the peripheral sensor through the input line, an instant of peripheral propagation $TP_j$ in which the pressoric wave reaches the predetermined peripheral section,
  calculating at least one value of an indicator parameter iHAT as a function of at least the instant of generation $TG_j$ and the instant of peripheral propagation $TP_j$,
  verifying whether or not said calculated value or values of the indicator parameter iHAT satisfy a reference criterion,
  determining whether a condition of hypovolemia is present or not in the subject depending upon the outcome of said verification.

In a fifty-sixth aspect according to the preceding aspect the control unit is configured for:
determining a temporal interval $\Delta T_j$ between a heartbeat and a following heartbeat, and calculating the indicator value parameter value iHAT as a function of at least:
the instant of generation $TG_j$,
the instant of peripheral propagation $TP_j$ and
the temporal interval $\Delta T_j$.

In a fifty-seventh aspect according to any one of the preceding two aspects the control unit is configured for:
determining an ECG chart from the signal coming from the electrodes; and
identifying the instant of generation $TG_j$ as a moment in which, in the ECG chart, a wave Rj relating to a sequence of waves $QRS_j$ exhibits a maximum peak.

In a fifty-eighth aspect according to any one of the preceding three aspects the peripheral sensor comprises a pulse oximeter and wherein the control unit is configured for:
determining a saturometer curve from the signal coming from the pulse oximeter and identifying the instant of peripheral propagation $TP_j$ by detecting a peak in amplitude of the saturometer curve.

In a fifty-ninth aspect according to any one of the preceding four aspects the value of the indicator parameter iHAT is a function of a temporal delay $\delta T_j$ occurring between the instant of generation $TG_j$ and the instant of peripheral propagation $TP_j$ divided by the time interval occurring between two successive heartbeats $\Delta T_j$.

In a sixtieth aspect according to any one of the preceding five aspects verifying comprises at least one of the following verification steps:
  verifying if the instant value of the indicator parameter iHAT is higher than a prefixed threshold value;
  verifying if a mean value of the indicator parameter iHAT is higher than a prefixed threshold value, the mean value of the indicator parameter being calculated as a mean of a plurality of instant values of the indicator parameter iHAT related to a plurality of successive heartbeats;
  verifying if the gradient of instant values of the indicator parameter iHAT changes across time beyond a prefixed threshold gradient;
  verifying if the gradient of mean values if $iHAT_{med}$ of the indicator parameter iHAT changes across time beyond a prefixed threshold gradient, each mean value of the indicator parameter being calculated as a mean of a plurality of instant values of the indicator parameter iHAT related to a plurality of successive heartbeats;
  verifying if the distribution of the instant values of the indicator parameter iHAT around their mean value changes across time beyond a prefixed distribution level;
and wherein determining whether a condition of hypovolemia is present or not comprises determining if one or more of the above verification steps is positively passed and in the affirmative concluding that hypovolemia exists in the subject.

In a sixty-first aspect according to any one of the preceding six aspects the control unit is further configured to calculating the amount of haemorrhage, optionally as blood volume fraction relative to the subject's total blood volume, as a function of the detected value of the indicator parameter (iHAT).

In a sixty-second aspect according to any one of the preceding seven aspects the control unit is further configured to calculating the amount of haemorrhage, expressed as blood volume fraction relative to the subject's total blood volume, as linear function of the detected value of the indicator parameter (iHAT).

In a sixty-third aspect according to any one of the preceding eight aspects the control unit is configured to temporally synchronise the ECG chart and the saturometer curve, the temporal synchronisation comprising relating values of the ECG chart and the saturometer curve to a same temporal axis.

In a sixty-fourth aspect according to any one of the preceding nine aspects the apparatus comprises at least a first input line for receiving the one or more electrical signals coming from the electrodes; at least a second input line, distinct from the first line, for receiving the signal coming from the peripheral sensor.

In a sixty-fifth aspect according to any one of the preceding ten aspects the control unit is configured to repeat the calculation of the value of the indicator parameter a plurality of times, in relation to a plurality of successive heartbeats.

In a sixty-sixth aspect according to any one of the preceding eleven aspects the control unit is configured to determine a mean value $iHAT_{med}$ of the indicator parameter, the mean value being calculated as a mean of a plurality of parameter values iHAT related to a plurality of successive heartbeats.

In a sixty-seventh aspect according to any one of the preceding twelve aspects the apparatus comprises an output device selected in the group of a viewing device and an acoustic device, the control unit being connected to the output device and being configured to:
  generate a control signal when a condition of hypovolemia in the patient has been determined, send the control signal the output device in order to provide an acoustic and/or a visual indication to an operator to indicate that the subject reached a condition of hypovolemia.

In a sixty-eighth aspect according to any one of the preceding thirteen aspects the control unit is configured:
form, on the viewing device, a plurality of viewing fields which are distinct from one another,
display on a field, of the viewing fields a temporally-synchronized graphic representation of the ECG chart and the pulse oximeter signal.

In a sixty-ninth aspect according to any one of the preceding fourteen aspects the control unit is configured to display, on a viewing field of a viewing device a graphic representation of a temporal progression of the indicator parameter value and/or of the mean indicator parameter value (iHAT; $iHAT_{med}$).

In a seventieth aspect according to any one of the preceding fifteen aspects the control unit is configured to represent fiduciary markers, e.g. in a differentiated way, which fiduciary markers respectively relate to and identify peaks Rj of the wave R in the ECG chart and to peaks Sj in the saturometer curve.

In a seventy-first aspect according to any one of the preceding sixteen aspects the control unit is configured to represent on a viewing field of a viewing device, in a first graphic mode, the instant value and/or the mean value of the indicator parameter when lower than the threshold, and in a second graphic mode, different to the first graphic mode, the instant value and/or the mean value of the indicator parameter iHAT; $iHAT_{med}$ when higher than the threshold.

In a seventy-second aspect according to any one of the preceding seventeen aspects the control unit is configured to compare at least one of the instant value of the indicator parameter and the mean value of the indicator parameter iHAT; $iHAT_{med}$ with a plurality of respective threshold values defining a series of potentially dangerous intervals.

In a seventy-third aspect according to the preceding aspect, the control unit is further configured to generate a respective control signal when each of the threshold values has been exceeded and to send each said respective control signal to an output device to inform an operator in a graphically and or acoustic different way when the subject reaches different levels of hypovolemia.

In a seventy-fourth aspect according to any one of the preceding nineteen aspects the threshold value to which the instant or the mean value of the indicator parameter (iHAT) is one of:
a predefined value comprised between 55% and 60%,
a predefined value substantially equal to 58%,
a calculated value the control unit (6) is configured to enable programming of.

A seventy-fifth aspect concerns an apparatus for determining a blood haemorrhage volume lost in a subject, comprising:
at least an input line for:
receiving one or more electrical signals coming from one or more electrodes predisposed to detect cardiac activity;
receiving a signal coming from a peripheral sensor predisposed to operate in a predetermined peripheral section of the subject's body;
a control unit connected to the input line and configured for:
determining, from the signal or signals coming from the electrodes through the line, an instant $TG_j$ in which a pressoric wave is generated in relation to a heartbeat,
determining, from the signal coming from the peripheral sensor through the input line, an instant of peripheral propagation $TP_j$ in which the pressoric wave reaches the predetermined peripheral section,
calculating at least one value of an indicator parameter iHAT as a function of at least the instant of generation $TG_j$ and the instant of peripheral propagation $TP_j$,
calculating the amount of haemorrhage volume as a function of the detected value of the indicator parameter iHAT.

In a seventy-sixth aspect according to the preceding aspect the haemorrhage volume is calculated by the control unit as blood volume fraction relative to the subject's total blood volume.

In a seventy-seventh aspect according to any one of the preceding two aspects said amount of haemorrhage volume is calculated as a linear function of the detected value of the indicator parameter iHAT.

In a seventy-eighth aspect according to any one of the preceding three aspects the control unit is configured for:
determining a temporal interval $\Delta T_j$ between a heartbeat and a following heartbeat, and a temporal delay $\delta T_j$ occurring between the instant of generation $TG_j$ and the instant of peripheral propagation $TP_j$ and
calculating the indicator value parameter value iHAT as a function of at least the temporal interval $\Delta T_j$ and the temporal delay $\delta T_j$.

In a seventy-ninth aspect according to any one of the preceding four aspects the peripheral sensor comprises a pulse oximeter.

In a eightieth aspect according to the preceding aspect the control unit is configured for:
determining a saturometer curve from the signal coming from the pulse oximeter and identifying the instant of peripheral propagation $TP_j$ by detecting a peak in amplitude of the saturometer curve.

In a eighty-first aspect according to any one of the preceding six aspects the control unit is configured to execute a verifying step the verifying comprises at least one of the following verification steps:
verifying if the instant value of the indicator parameter iHAT is higher than a prefixed threshold value;
verifying if a mean value of the indicator parameter iHAT is higher than a prefixed threshold value, the mean value of the indicator parameter being calculated as a mean of a plurality of instant values of the indicator parameter iHAT related to a plurality of successive heartbeats;
verifying if the gradient of instant values of the indicator parameter iHAT changes across time beyond a prefixed threshold gradient;
verifying if the gradient of mean values if $iHAT_{med}$ of the indicator parameter iHAT changes across time beyond a prefixed threshold gradient, each mean value of the indicator parameter being calculated as a mean of a plurality of instant values of the indicator parameter (iHAT) related to a plurality of successive heartbeats;
verifying if the distribution of the instant values of the indicator parameter (iHAT) around their mean value changes across time beyond a prefixed distribution level; the distribution can be calculated as variance or as standard deviation or using any other mathematical expression determining the dispersion of values around their mean value.
and wherein determining whether a condition of hypovolemia is present or not comprises determining if one or more (for instance to increase safety and accuracy two or three or four or all the hove criteria could be calculated) of the above verification steps is positively passed and in the affirmative concluding that hypovolemia exists in the subject.

A eighty-second aspect concerns a method for determining conditions of hypovolemia in a subject, comprising:

receiving one or more electrical signals coming from one or more electrodes 3 predisposed on a subject to detect cardiac activity;

receiving a signal coming from a peripheral sensor predisposed to operate in a predetermined peripheral section of the subject's body;

determining, from the signal or signals coming from the electrodes an instant $TG_j$ in which a pressoric wave is generated in relation to a heartbeat, determining, from the signal coming from the peripheral sensor, an instant of peripheral propagation $TP_j$ in which the pressoric wave reaches the predetermined peripheral section, calculating at least one value of an indicator parameter iHAT as a function of at least the instant of generation $TG_j$ and the instant of peripheral propagation $TP_j$, based on the at least one value of an indicator parameter iHAT determining at least one of:

the amount of haemorrhage volume in the subject as a function of the detected value of the indicator parameter iHAT;

whether a condition of hypovolemia is present or not in the subject depending upon the outcome of a verification if the calculated value or values of the indicator parameter iHAT satisfy a reference criterion.

In a eighty-third aspect according to the preceding aspect the method may be implemented using an apparatus according to any one of aspects from the first to the eighty-first.

In a eighty-fourth aspect according to any one of the preceding two aspects, the method comprises:

determining a temporal interval $\Delta T_j$ between a heartbeat and a following heartbeat, and a temporal delay $\delta T_j$ occurring between the instant of generation $TG_j$ and the instant of peripheral propagation $TP_j$ and calculating the indicator value parameter value iHAT as a function of at least the temporal interval $\Delta T_j$ and the temporal delay $\delta T_j$.

In a eighty-fifth aspect according to any one of the preceding three aspects, the method comprises:

determining an ECG chart from the signal coming from the electrodes; and identifying the instant of generation $TG_j$ as a moment in which, in the ECG chart, a wave Rj relating to a sequence of waves $QRS_j$ exhibits a maximum peak.

In a eighty-sixth aspect according to any one of the preceding four aspects, the peripheral sensor comprises a pulse oximeter and wherein the method comprises:

determining a saturometer curve from the signal coming from the pulse oximeter and identifying the instant of peripheral propagation $TP_j$ by detecting a peak in amplitude of the saturometer curve.

In a eighty-seventh aspect according to any one of the preceding five aspects, comprising calculating the value of the indicator parameter iHAT is a function of a temporal delay $\delta T_j$ occurring between the instant of generation $TG_j$ and the instant of peripheral propagation $TP_j$ divided by the time interval occurring between two successive heartbeats $\Delta T_j$.

In a eighty-eight aspect according to any one of the preceding six aspects, said verification comprises at least one of the following verification steps:

verifying if the instant value of the indicator parameter iHAT is higher than a prefixed threshold value;

verifying if a mean value of the indicator parameter iHAT is higher than a prefixed threshold value, the mean value of the indicator parameter being calculated as a mean of a plurality of instant values of the indicator parameter iHAT related to a plurality of successive heartbeats;

verifying if the gradient of instant values of the indicator parameter iHAT changes across time beyond a prefixed threshold gradient;

verifying if the gradient of mean values $iHAT_{med}$ of the indicator parameter iHAT changes across time beyond a prefixed threshold gradient, each mean value of the indicator parameter being calculated as a mean of a plurality of instant values of the indicator parameter iHAT related to a plurality of successive heartbeats;

verifying if the distribution of the instant values of the indicator parameter iHAT around their mean value changes across time beyond a prefixed distribution level;

and wherein determining whether a condition of hypovolemia is present or not comprises determining if one or more of the above verification steps is positively passed and in the affirmative concluding that hypovolemia exists in the subject.

In a eighty-ninth aspect according to any one of the preceding seven aspects comprising calculating the amount of haemorrhage, expressed in term of blood volume fraction relative to the subject's total blood volume, as a function of the detected value of the indicator parameter (iHAT), wherein said amount of haemorrhage is calculated as a linear function of the detected value of the indicator parameter (iHAT).

In a ninetieth aspect according to any one of the preceding seven aspects the method comprises:

repeating the calculation of the value of the indicator parameter a plurality of times, in relation to a plurality of successive heartbeats;

determining a mean value ($iHAT_{med}$) of the indicator parameter, the mean value being calculated as a mean of a plurality of parameter values (iHAT) related to a plurality of successive heartbeats.

In a ninety-first aspect a data carrier is provided comprising instructions which when executed by the control unit of an apparatus according to any one of the preceding apparatus aspects render said control unit configured to execute the respective steps described in the preceding aspects.

BRIEF DESCRIPTION OF THE DRAWINGS

A brief description of the drawings will now be given, which drawings are provided by way of non-limiting example. In particular:

FIG. 10 is a table summarizing a test conducted to show the variation of the value of the iHAT index on subjects submitted to simulated haemorrhage.

DETAILED DESCRIPTION

With reference to the figures, 1 denotes in an apparatus for determining conditions of hypovolemia in a subject, for example a patient for whom the presence of the conditions of hypovolemia is to be determined without using invasive instruments or procedures. The apparatus 1 comprises at least a first input line 2 for receiving one or more electric signals coming from one or more electrodes 3 predisposed to detect the cardiac activity of a subject or patient P. In the illustrated embodiment three electrodes 3 are comprised, two of which are associated to the thorax of the patient P subjected to monitoring and one of which is associated to the abdominal area. The electrodes can be connected to the first input line 2 with respective wires or alternatively via a wireless connection.

A second input line 4 receives a signal coming from a peripheral sensor 5 operating at a predetermined peripheral section of the patient's body P.

Figure 3:
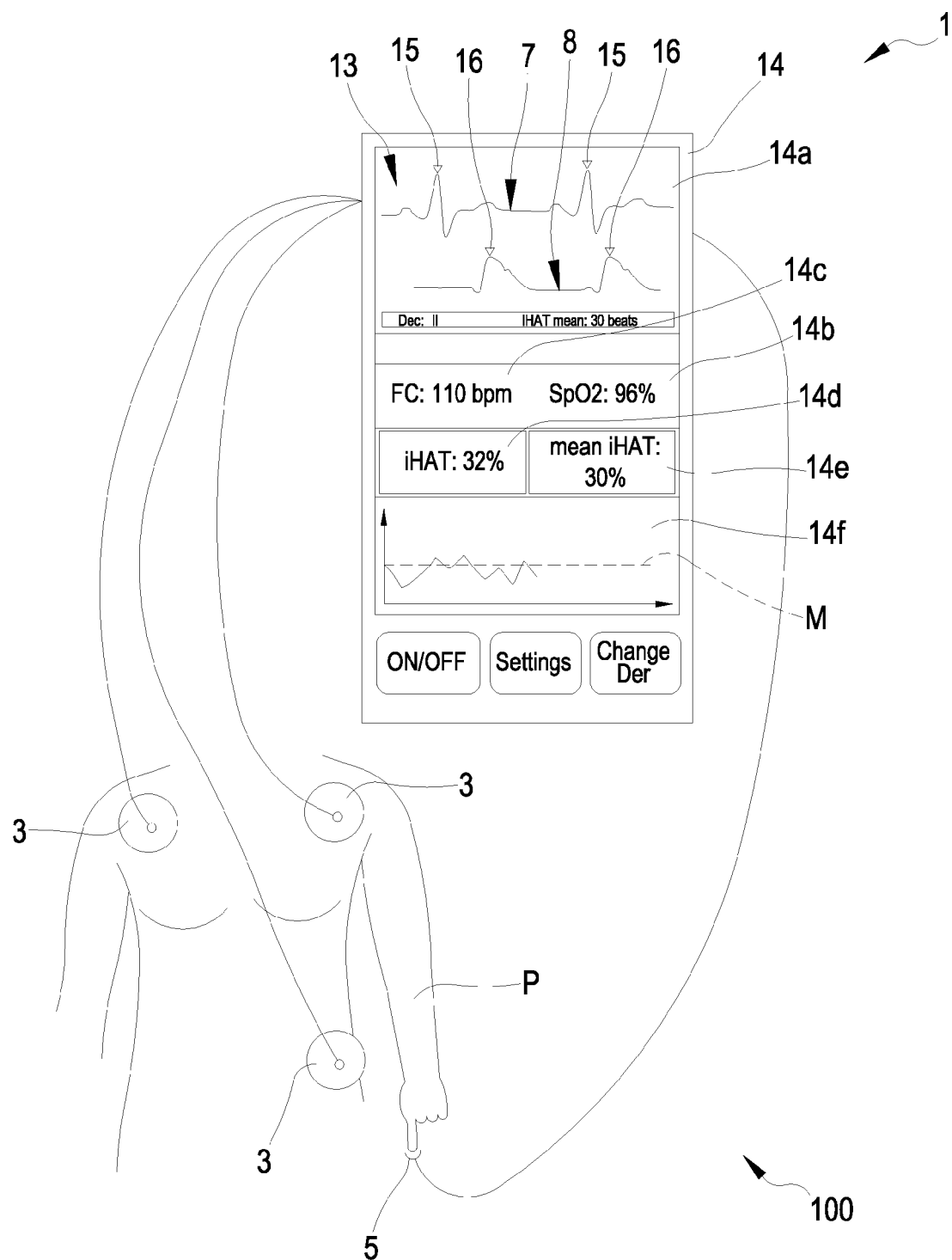
FIG. 3 is a schematic view of the assembly showing an identification system for the identification of parameter indicative of hypovolemia in a patient.

As illustrated in FIG. 3, the peripheral sensor 5 can for example be associated to a patient's finger (for example the index finger), to a patient's earlobe, or to another peripheral portion of the patient's body P. The system of electrodes 3, peripheral sensor 5 and device 1 is denoted by reference numeral 100.

The first input line 2 is connected to a control unit, for example an analog unit, or a micro-processor, denoted by 6 in the drawings. The control unit is configured to receive a signal from the first input line 2 and to determine, on the basis of the signal, an electrocardiograph chart (ECG) 7 comprising a temporal representation of an amplitude of an electrical signal emitted by the heart muscle. The control unit 6 is also configured such as to identify, on the ECG chart, an instant $TG_j$ of generation of the pressoric wave in relation to the heartbeat. In particular this instant of generation is identified as the moment in which the ECG chart exhibits a maximum point in the wave Rj in relation to a wave sequence (QRS)j; the "j" here indicates that what is described, relates to the cycle j in a series of successive cycles each corresponding to a heartbeat.

The second input line is also connected to the control unit 6. In particular the peripheral sensor 5 comprises a pulse oximeter and the control unit is configured such as to receive in input, via the second line 4, an electric signal coining from the pulse oximeter; the control unit is further configured and such as to determine from the second signal a saturometer curve 8 (also denoted by $S_pO_2$) which is a representation of the oxygen concentration vs. time as detected by the pulse oximeter. From the signal coming from the second input line, the control unit determines the curve 8 and identifies an instant of periphery propagation $TP_j$ in which the pressoric wave generated by the heartbeat reaches the peripheral section in which the peripheral sensor works 5. In the case shown in the attached drawings, the instant of peripheral propagation $TP_j$ is identified by detecting a peak in the amplitude of the saturometer 8 curve.

The control unit 5 may also be configured to calculate the value of an indicator parameter (denoted by iHAT in the accompanying figures and being indicative of conditions of hypovolemia in the patient as it will be hereinafter discussed) which is a function of both the instant of peripheral propagation $TP_j$ and the instant of generation $TG_j$. In particular, in a same heartbeat the indicator parameter if iHAT is calculated as a function of both the instant of generation and the instant of peripheral propagation. More precisely, the control unit is configured such as to determine a temporal interval $\Delta T_j$ between a heartbeat and a successive heartbeat and such as to calculate the value of the indicator parameter as a function of the instant of generation $TG_j$, the instant of peripheral propagation $TP_j$ and the temporal interval $\Delta T_j$ between a heartbeat and a following heartbeat.

Figure 1:
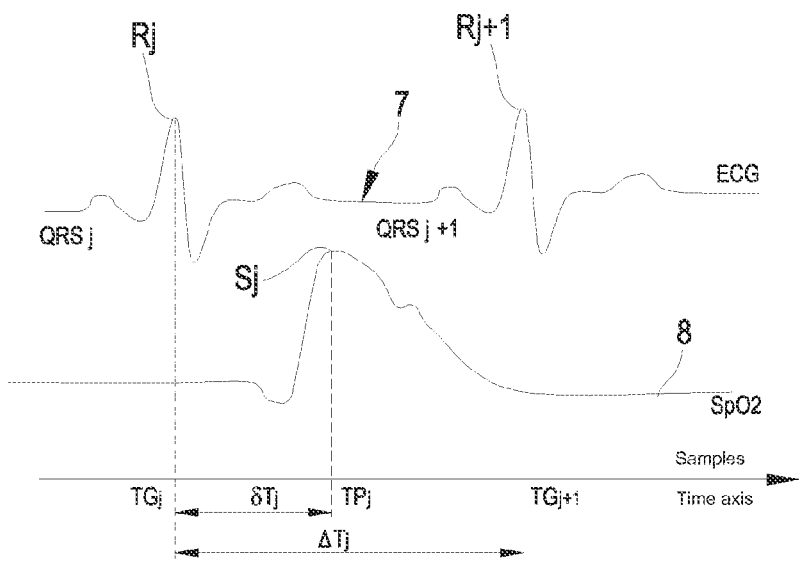
FIG. 1 is a schematic view of the chart provided, by an electrocardiograph (ECG) and a pulse oximeter.

Still more precisely, with reference for example to FIG. 1, the control unit is able, for each heartbeat i.e. for each cycle occurring between the peak $R_j$ and the following peak $R_{j+1}$ in the ECG chart, to determine the time interval $\Delta T_j$ between $R_j$ and $R_{j+1}$ as well as the time delay $\delta T_j$ between the instant of propagation $TP_j$ in which the peak $S_j$ occurs in the saturometer curve and the instant of generation $TG_j$.

The value of the indicator parameter iHAT is thus calculated using the formula:

$$iHAT=(TP_j-TG_j)/(TG_{j+1}-TG_j)=\delta T_j/\Delta T_j$$

The control unit 6 is configured to repeat a plurality of times, in a cycle, the calculation of the value of the indicator value for a plurality of successive heart cycles j (i.e. a plurality of successive heartbeats).

Figure 5:
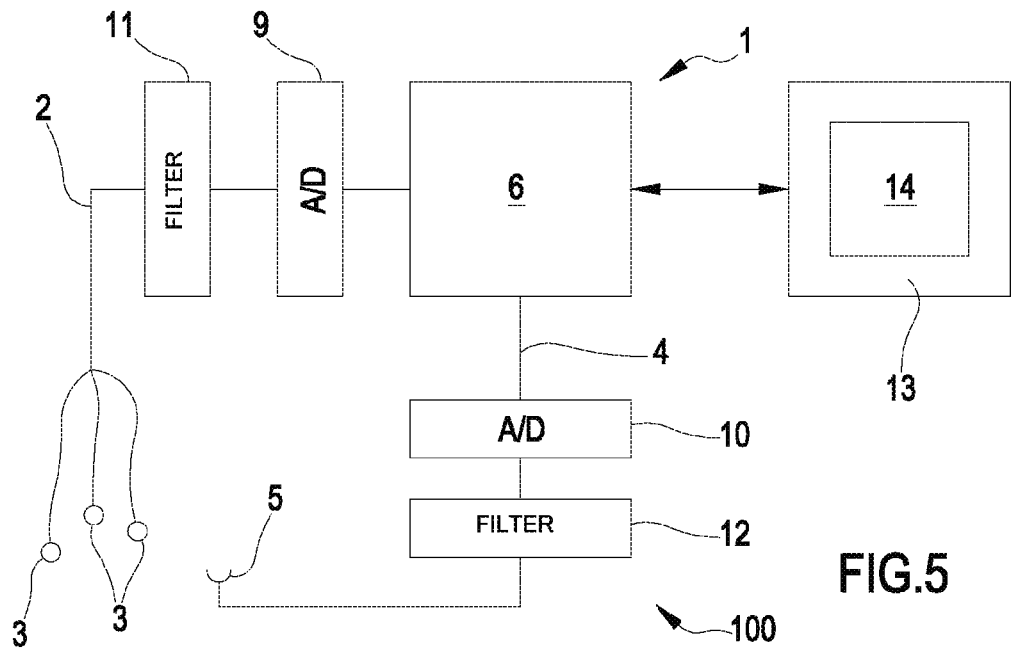
FIG. 5 is a block diagram of the system of FIG. 3.

As can be seen in FIG. 5, analog-digital converters 9 and 10 are included on the input lines 2 and 4, for converting the electrical signals in arrival from the electrodes and from the peripheral sensor, in digital signal form.

The electrical signals are sampled at a respective frequency, typically 300 Hertz or more. The control unit 6 is configured such as to temporally synchronise the first and second signal as in FIG. 1, such that both the signal arriving from the first input line and forming the ECG chart and the signal coming from the second input line and forming the saturometer curve relate to a same temporal axis such that independently of when the indicator parameter is calculated, the peaks $R_j$, $R_{j+1}$ and $S_j$ described, refer to a same interval $\Delta T_j$ i.e. a same cardiac cycle.

With reference to FIG. 5, in which a block diagram of an apparatus 1 is illustrated, the apparatus 1 can also comprise one or more filters 11 active on the signal coming from the electrodes 3 and one or snore filters 12 active on the signal coining from the peripheral sensor.

These filters can be implemented both upstream of the analog-digital conversion block 9, 10 (as illustrated in FIG. 5) and downstream thereof. In particular at least a first filter can be provided active on the signal coming from the electrodes 3 for filtering the noise due to feeding, a second filter active once more on the signal coming from the electrodes 3 for filtering the noise to any tremor of the patient and a third filter active on the signal from the electrodes for filtering the noise due to the patient's breathing.

The three above-described filters are configured to cut or considerably reduce typical frequencies of feeding noise, the noise due to a patient's tremor and the noise caused by the patient's breathing.

Likewise, a first filter, a second filter and a third filter acting on the signal coming from the peripheral sensor 5 can be provided respectively for filtering the noise due to feeding, the noise due to a patient's tremor and the noise caused by the patient's breathing.

As mentioned, the calculation of the value of the indicator parameter is repeated a plurality of times cyclically, thus obtaining a value for the indicator parameter for a plurality of successive heartbeats.

The control unit 6 may be configured to determine both an instantaneous value of the indicator parameter for each heartbeat and a mean value of the indicator value, calculated as a mean of the instant values across a plurality of successive heartbeats.

The control unit 6 may be configured to verify whether the value of the indicator parameter (for example the instant value or the mean value of the indicator parameter) exceeds a respective threshold value. In the affirmative the control unit may be configured to generate a signal, such as a warning signal to the operator or a command signal designed to activate further specific functions.

Figure 4:
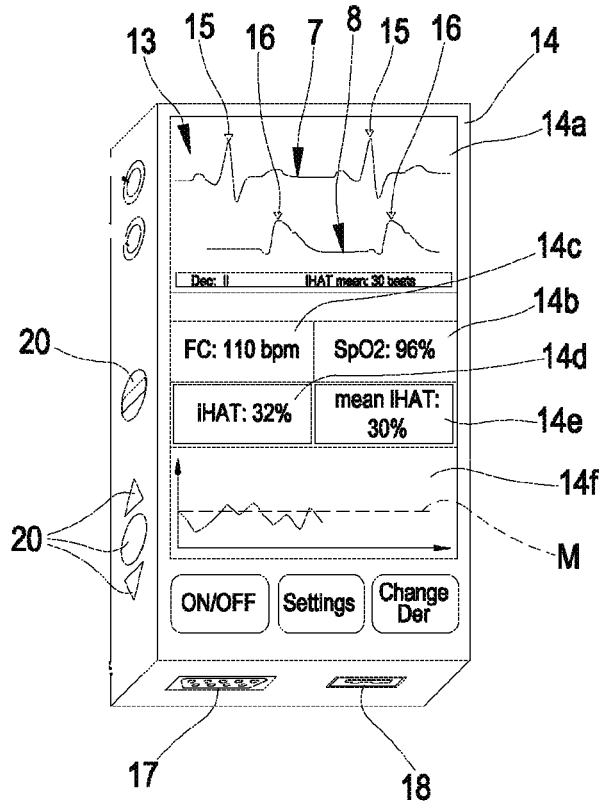
FIG. 4 is a detail relating to an example of a device that is part of the system of FIG. 3, usable for instance to determine conditions of hypovolemia.

As can be seen in FIG. 5, and as shown in FIGS. 3 and 4, the apparatus 1 comprises a user interface 13 having at least a viewing device 14; the interface 13 is connected to the control unit and the viewing device 14 is controlled by the unit 6: the control unit 6 may be configured to provide a visual signal (possibly combined with an acoustic signal) when the instant value and/or the mean value of the indicator parameter exceed the threshold value.

For example, should the instant value and/or the mean value of the indicator value exceed the threshold vale, the control unit 6 may determine that the value be visualized in a graphic inode that is different from the conditions in which the threshold value is not exceeded: for example, in a different colour with respect to that used for representing the value of the indicator value when lower than the threshold.

The viewing device 14 can comprise a plurality of fields: a first field 14a in which the ECG chart and the saturometer curve are shown, a second field 14b in which the instant value of the oxygen saturation is represented, a third field 14c in which the instant value of the heartbeat frequency is represented, a fourth field 14d in which the instant value of the indicator value is shown, a fifth field 14e in which the mean value of the indicator value is shown (in FIGS. 3 and 4 these values are expressed in percentages), a sixth field 14f in which a graphic representation of the time progression of the indicator parameter is supplied as well as a representation of the maximum threshold M. The visual appearance of at least one of the fields 14d, 14e, 14f can be automatically varied by the control unit 6 when the threshold is exceeded.

Normally the threshold value beyond which a patient is considered to be in a state of hypovolemia, or which at least deserves attention from a medical specialist, is 58% (or 0.58 should the value of the indicator parameter be expressed in decimal form).

In the examples of FIGS. 3 and 4, the values of the indicator parameter are 32% (instant value) and 30% (mean value calculated on a plurality of instant values): in this case the graphic representation of these values on the display is for example done in a first colour. Should the values exceed 58% the control unit is programmed to change the colour of the background of the field in which the indicator parameter values are shown and/or the colour of the wording representing the instant value of the indicator value, or another graphic aspect of the fields in which the values are represented, giving the user a clear signal of a state of potential risk.

For example, to attract the user's attention the above fields can be sharply illuminated or evidenced such that the difference between a non-threshold-exceeding condition and an exceeding one is clear.

Still in reference to the threshold value, it is note-worthy that the apparatus 1 may comprise a unit 6 with configured such that the threshold value can be programmed.

There might be a plurality of possible threshold values, for example 55%, 57%, 59% in relation to various levels of conditions of hypovolemia and thus gravity of situation.

The control unit can also be able to receive at least an additional parameter, such as the age of the patient or subject undergoing monitoring, and can therefore determine the threshold value or values as a function of the age of the subject, such as to adapt the control system to the characteristics of the patient under examination.

Still with reference to FIGS. 3 and 4, the control unit is configured such as to visualise, in the field 14a, a graphic representation of the ECG charge and the pulse oximeter signal.

In particular, in the examples of FIGS. 3 and 4, the ECG chart and the saturometer curve are represented in a same viewing field and are temporally synchronised such as to offer the user an intuitive view of the progression of the ECG signal and the pulse oximeter signal; the control unit may be further configurable to show a differentiated view of fiduciary markers 15, 16 relating respective to peaks of the wave R of the ECG chart and the peaks of the saturometer curve.

In the examples of FIGS. 3 and 4, the fiduciary markers are represented by graphic elements configured for example as a triangle, which show when, at each pulse, the instant of generation and the instant of propagation are taken which are used for the calculation of the value of the indicator parameter.

Still with reference to the figures of the drawings, in particular FIG. 4, note that the device 1 is also provided with interfaces for entering data or collecting data, for example interfaces of the RS232 or USB type, respectively denoted by 17 and 18.

The apparatus 1 may also be provided with a control keyboard 19 comprising one or more buttons 20 for selecting and confirming input by the user.

Following the above prevalently structural description, there now follows an example of a procedure, for example a procedure that can be performed by the control unit 6 with the aim of calculating the value of the indicator parameter.

Figure 2:
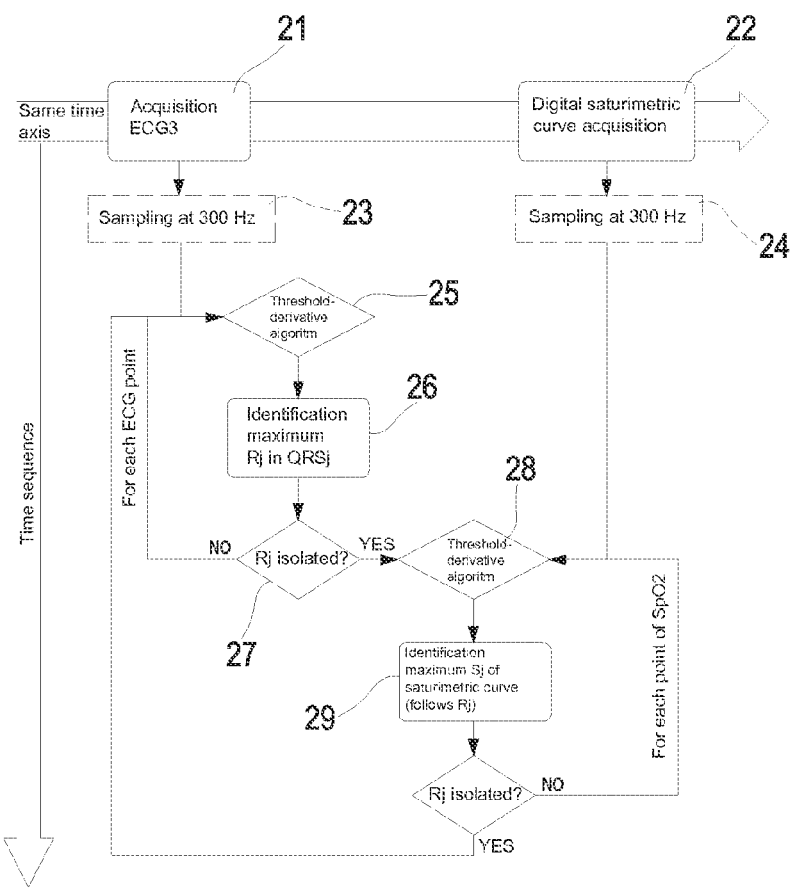
FIG. 2 is a flow chart of a process of one embodiment described herein.

Reference will now be made in particular to the example of FIG. 2. The chart of FIG. 2 shows a non limiting example of a sequence of steps (which may be implemented by control unit 6) for isolating at each cardiac cycle j the corresponding Rj and Sj.

In a first step 21, an ECG chart is composed, for example by using a sensor system with three or more electrodes.

The saturometer curve (step 22) is also set up.

In a third phase 23 the ECG chart and the saturometer curve are sampled (steps 24 and 25) for example at 300 hertz, and then, for example using an algorithm of the threshold-derived type, the maximum point $R_j$ is derived of a sequence $(QRS)_j$ relating to the jth pulse (step 26).

The algorithm performed by the control unit then verifies if a maximum peak $R_j$ (step 27) has been found and if so a further algorithm is applied of the threshold-derived type (step 28) for identifying the maximum peak of the saturometer curve (step 29 which temporally follows step 26 of identification of the maximum peak $R_j$).

The algorithm comprises the verification of the identification of the peak Sj of the saturometer curve and if successful the control unit 6 has two working points Rj and Sj necessary, with reference to the jth period relating to the jth pulse, for calculating the indicator parameter.

The above-described algorithm is repeated for the j+1 cycle, substantially as described herein above.

As the evaluation of the maximum peak $S_j$ of the saturometer curve is performed following the identification of the maximum peak Rj of the ECG chart, there is a substantial guarantee that maximums $S_j$ and maximums $R_j$ are compared, which are relative to a same pulse, thus avoiding errors in calculation of the value of the indicator parameter.

The times at which Rj and Sj are identified are then used to calculate the delay between Rj and the corresponding Sj: this delay $\delta T_j$ together with the time interval $\Delta T_j$ between two consecutive Rj, Rj+1 are used to calculate the indicative parameter value iHAT=$\delta T_j/\Delta T_j$.

Although the above examples describe the case where the measured value or values of the indicator parameter are compared with one or more thresholds to verify whether or not there is presence of a condition of hypovolemia, it should be noted that it is possible determining the presence of a condition of hypovolemia using one or more values of the ic indicator parameter iHAT and verifying said values against a predetermined verification criterion.

More in detail according to one embodiment, a procedure for determining an indicator parameter indicative of presence of a condition of hypovolemia in a subject, may comprise the steps of:

connecting a plurality of electrodes to the skin of a subject in order to detect electric signals determined by cardiac activity, connecting at least a peripheral sensor to the subject at a predetermined peripheral section of the subject's body (for example a pulse oximeter sensor associated to a finger or ear), receiving one or more signals coming from the electrodes and a signal coming from the peripheral sensor,
determining, from the signal or signals coining from the electrodes, an instant $TG_j$ in which a pressoric wave is generated relating to a heartbeat,
determining, from the signal coming from the peripheral sensor, an instant of peripheral propagation $TP_j$ in which the pressoric wave reaches the predetermined peripheral section of the body of the subject subjected to monitoring,
determining a temporal interval $\Delta T_j$ between a heart beat and a successive heart beat,
determining the temporal delay $\delta T_j$ between the instant of generation $TG_j$ and the instant of peripheral propagation $TP_j$,
calculating at least one value of the indicator parameter iHAT by dividing $\delta Tj$ by the time interval between the two successive heartbeats $\Delta T_j$,
verifying whether or not said calculated value or values satisfy a reference criterion,
determining whether a condition of hypovolemia is present or not in the patient depending upon the outcome of said verification.

The above procedure can be executed using the system shown in the appended drawings comprising electrodes, a peripheral sensor and a control unit configured for collecting the various signals from the electrodes and from the peripheral sensor and for performing the above steps of determining and verifying.

The reference criterion, which may be stored in a memory connected or associated to the control unit, may be one of the following:

The passing of a threshold as described in the detailed description: in other words if the instant value of the indicator parameter or if the mean value of the indicator parameter iHAT is higher than a certain prefixed threshold value than the verification is positive and it is determined that a condition of hypovolemia exists. In this case the control unit is configured to generate a signal, such as a warning or to alter display of certain information on the visualization unit, as above described;

A second alternative criterion comprises verifying if the trend of the instant values or of the mean value of the indicator parameter iHAT remains substantially constant or changes across time; for instance the derivative or gradient with respect to time of the iHAT may be calculated and when said derivative or gradient changes above a certain respective threshold gradient, then the verification is positive and it is determined that a condition of hypovolemia exists.

A third alternative criterion comprises verifying if the distribution of the instant values of the indicator parameter iHAT around their mean value remains constant or changes across time; the distribution of the instant values of iHAT around the iHAT mean value can calculated by using any method, such as by way of non limiting example by calculating the variance or by calculating the standard deviation of said instant values of the iHAT. If the standard deviation is verified to be higher than a certain distribution level, then it is concluded that there is a situation of hypovolemia exists in the patient.

It is also possible to executed two or all the above criteria in order to have the highest degree of accuracy in the determination of presence of hypovolemia.

According to a further aspect, the indicator parameter may be used to estimate the hemorrhage amount. Indeed, the applicant uncovered that the correlation between iHAT and hemorrhage was significant. Moreover, onset of iHAT variation was observed in tests conducted on swine after 90 ml blood withdrawal, thus iHAT could be used in monitoring the early phases of hemorrhage and to quantify the amount of hemorrhage.

Figure 9:
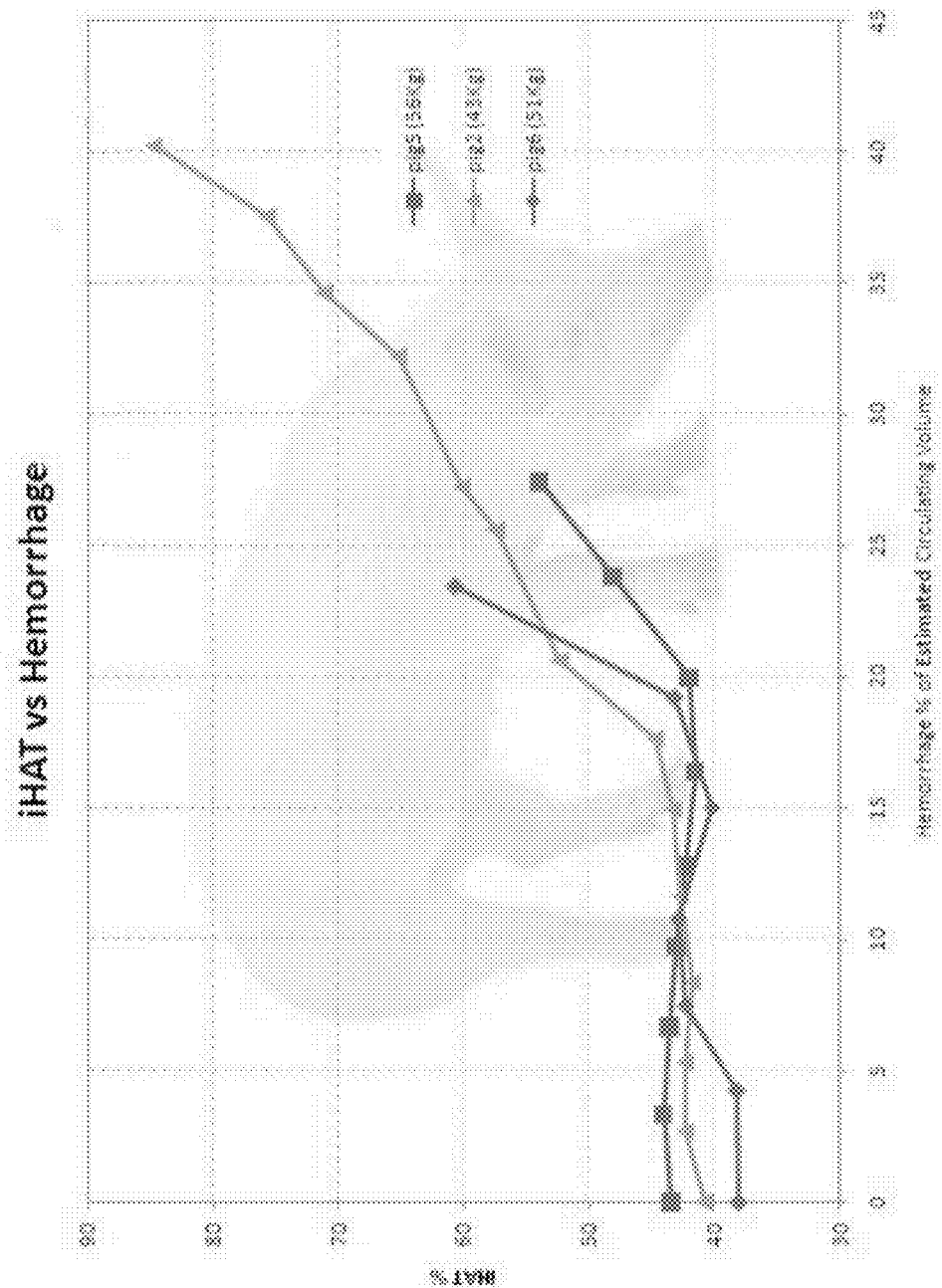
FIG. 9 shows the variation of the index iHAT for the tested swine expressed as a percentage vs. the haemorrhage volume expressed as percentage of the total blood volume of the subject.

As it can be seen from FIG. 9, haemorrhage amount, expressed as blood volume fraction relative to the subject's total blood volume, is a function of the detected value of the indicator parameter (iHAT). In particular, above about 15% (see FIG. 9), the amount of haemorrhage (expressed as fraction or percentage of total blood volume circulating in the patient) may be calculated as a linear function of the detected value of the indicator parameter (iHAT):

$$\text{Haemorrhage Volume/Total Blood Volume} = K * i\text{HAT}$$

Validation Tests

Test 1

Objective of this test was to confirm new index of hypovolemia (iHAT) tracks autonomic function during simulated hemorrhage in humans.

Subjects 9 healthy non smoking volunteers (2 males, 7 females, aged 23-38 mean age 29) have been enrolled in the protocol. Subjects were asked to refrain from caffeine beverages and alcohol assumption at least 12 h before the trial. The subjects were also asked not to undertake any intensive exercise in the 12 h before the study.

Interventions

Progressive lower body negative pressure (LBNP) was applied in 5-min stages until the onset of impending cardiovascular collapse. Lower body negative pressure (LBNP) is a well established research technique with many uses (see William H. Cooke, PhD; Caroline A. Rickards, PhD; Kathy L. Ryan, PhD; Victor A. Convertino, PhD.—Autonomic compensation to simulated hemorrhage monitored with heart period variability. Crit Care Med 2008 Vol. 36, No. 6, which is herein incorporated by reference). LBNP is most often used as a cardiovascular stressor to simulate gravitational stress, hemorrhage, to alter preload and manipulate baroreceptors. During LBNP the legs of the volunteers are sealed at the level of the iliac crest (in a supine position) in a LBNP Chamber (see Ben T. A. Esch, Jessica M. Scott and Darren E. R. Warburton. Construction of a lower body negative pressure chamber, Advan in Physiol Edu 31:76-81, 2007, which is herein incorporated by reference). Air pressure inside the chamber is then reduced by a vacuum pump. Blood shifts from areas of higher pressure (upper body maintained outside the chamber toward the legs (at a lower pressure). Until physiological compensation is working properly blood is stored in capacitance vessel and vasoconstriction and tachycardia are present. Inadequate compensation leads to Blood pressure falling and syncope.

Measurement Protocol

The subject initially rested in a supine position in the LBNP Chamber for a period of 10 minutes. The subject's feet were supported by a footboard, and straps were applied at the levels of waist and shoulders to stabilize the body during LBNP. Measurements were made at each of the following negative pressures in incremental order: 0, −15, −30, −45, −60, −70, and −80 or until impending collapse.

Systolic Blood pressure (SBP), Diastolic (DBP), Heart Rate (HR) were recorded every minute. Beat-by-beat iHAT was calculated offline.

Results

Application of lower body negative pressure caused progressive increases of iHAT, and heart rate. Blood pressures changed minimally and late. iHAT increased from 37.2% to 42.5%, 48.3%, 49.6% respectively at 0, −30, −45 and −60 mmHg of LBNP applied 8 ($p<0.05$)—see table "Results" reported in FIG. 10. Correlation between iHAT and LBNP was R2=0.978, $p<0.05$. AUC of iHAT ROC curve when employed to anticipate presyncopal symptoms was 0.911 ($p<0.01$) (Sensitivity 90%, Sensibility 78.4%).

Conclusions iHAT tracks early compensatory autonomic and hemodynamic responses to progressive reduction in central blood volume. iHAT may contribute to early assessments of the magnitude of blood volume loss during hemorrhage.

Test 2: SWAT (SWine Heart to Arm Time) Protocol

A large danish swine (44 Kg) was maintained under general anaesthesia with Sevorane 2% and Cisatracurium infusion at 6 mg/h after premedication with tiletamine/zolazepam 5 mg/kg, medetamine 0.025 mg/kg and atropine 0.05 mg/kg with a single lateral neck injection, and induction by propofol 2.5 mg/kg, ECG and PPG (measured at the tongue) were continuously recorded to calculate iHAT offline. An arterial Pulsion PiCCO catheter was placed in the left femoral artery.

Hemorrhage was induced at a rate of 0.8 ml/kg/min, to 27.6% of total blood volume in 24 minutes, and stopped after 500 and 700 ml for PiCCO system recalibration. PiCCO hemodynamic parameters and invasive blood pressure were recorded each minute.

Arterial blood gases, haematocrit (HT), haemoglobin (Hb) and lactates were measured at baseline, after 500 ml and after 700 ml blood withdrawal.

Figure 6:
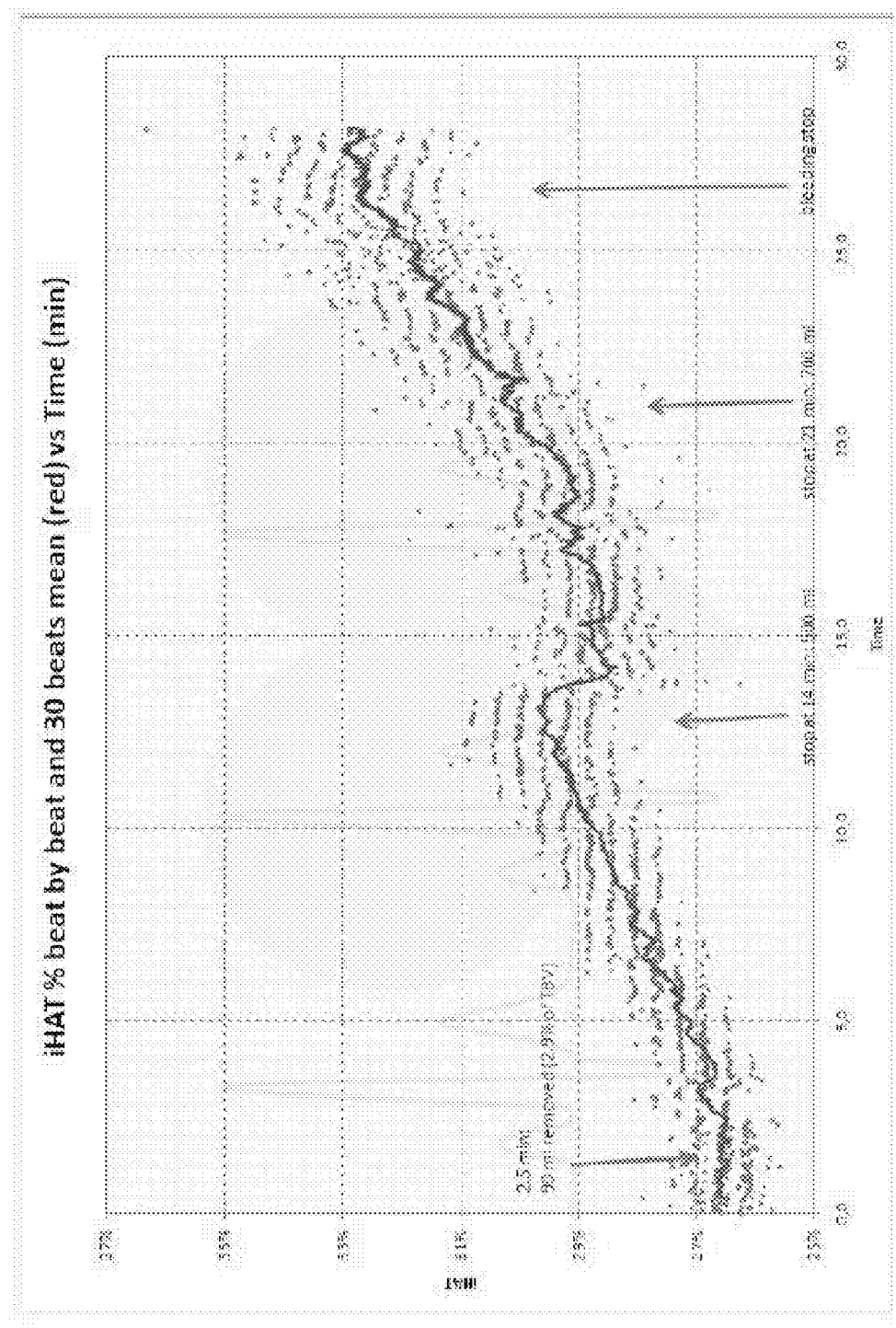
FIG. 6 shows the variation of an index, the iHAT index, beat by beat and of its 30 beat mean value vs. time.

The instant iHAT % values recorded beat by beat and the 30 beats mean value of the iHAT % indicator parameter are reported in FIG. 6, which is a representation of iHAT % vs. time. As it can be seen the iHAT % is very responsive to an hemorrhage condition. After 90 ml of induced hemorrhage, the absolute value of the iHAT and also the derivative of the iHAT vs. time initiated to increase. From FIG. 6 it can also be noticed that the standard deviation of the instant values of the iHAT from the mean value of the iHAT progressively increases with time (i.e. with an increase in the hemorrhage volume).

Figure 7:
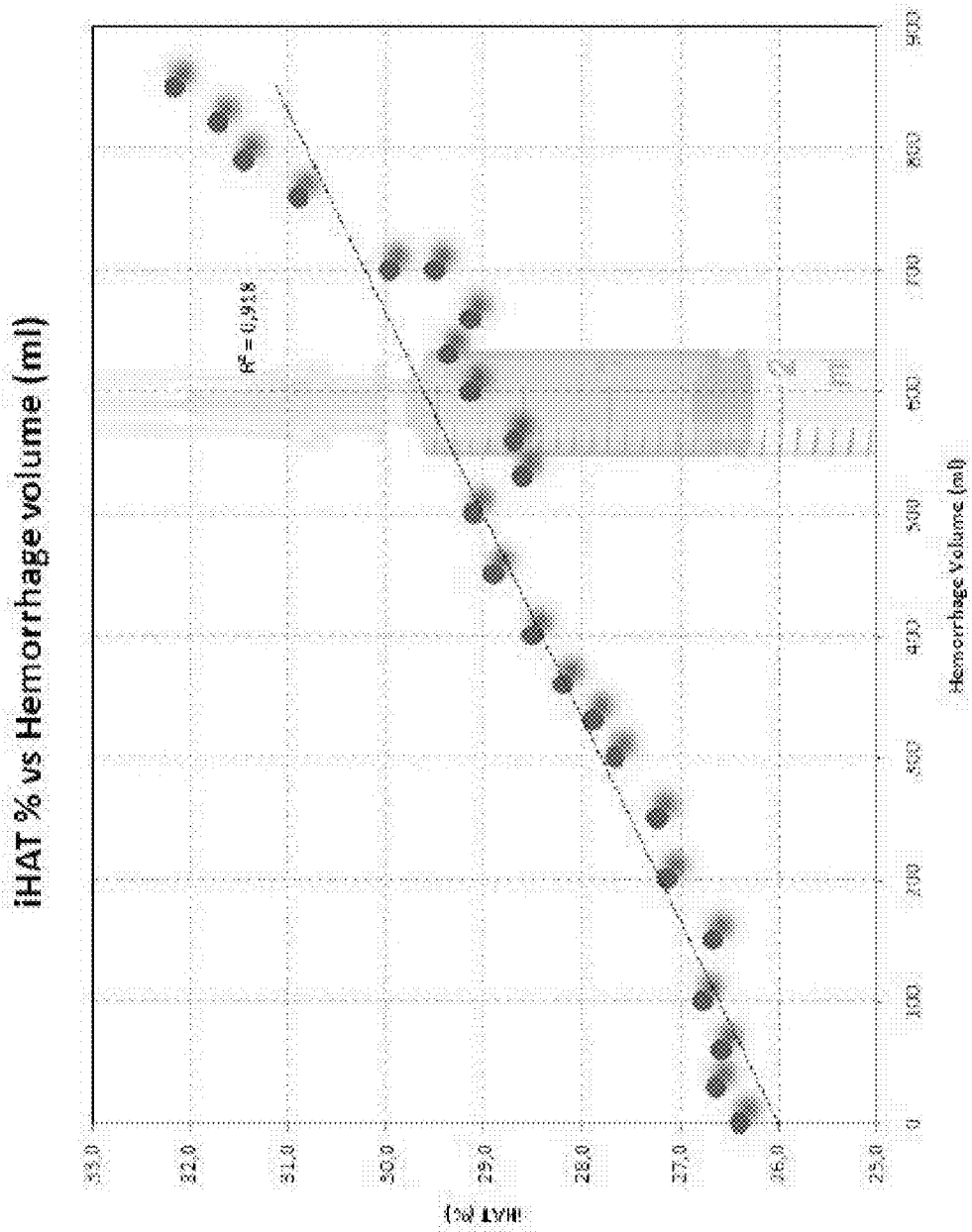
FIG. 7 shows the variation of the index iHAT expressed as a percentage vs. the haemorrhage volume expressed as percentage of the total blood volume of the patient.
Figure 8:
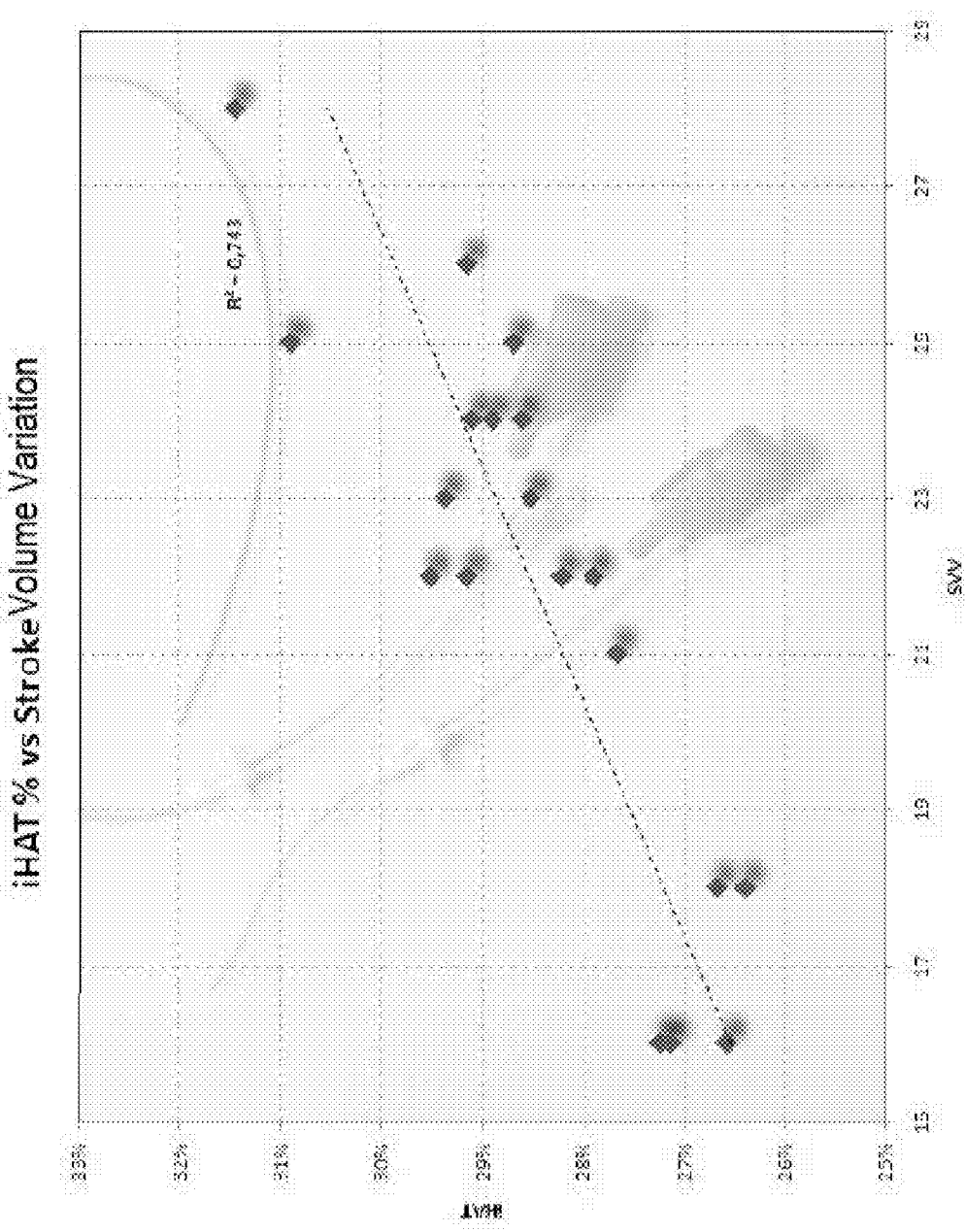
FIG. 8 shows the variation of the index iHAT expressed as a percentage vs. the subject's cardiac stroke volume.

As visible from FIGS. 7 and 8, which again refer to the same swine test, the indicator parameter may be used to estimate the hemorrhage amount. Indeed, the correlation between iHAT (averaged on 30 beats) and hemorrhage is significant ($R^2=0.904$, $p<0.001$), see FIG. 7. The correlation between iHAT (averaged) and stroke volume variation (SVV) is also significant ($R^2=0.743$, $p<0.05$), see FIG. 8. Moreover, onset of iHAT variation is prompt after 90 ml blood withdrawal whereas SVV and PPV changed only after 150 ml blood loss, iHAT could be used in monitoring the early phases of hemorrhage.

Test 3

SWAT protocol of Test 2 was then applied on 3 consequent large Danish pigs measuring iHAT at a more peripheral site than the tongue. The ear was used to detect PPG curve. This should allow bigger variations (and a higher sensibility in tracking hemorrhage). In fact data show that a 5% variation in iHAT (relatively to iHAT at baseline) is effective in tracking a hemorrhage below 20% of total blood volume. All 3 large danish pigs behave the same way with a linear relationship between iHAT and the percentage of hemorrhage after 20% of blood loss, see FIG. 9. This means that iHAT may be used to estimate blood loss.

The apparatus and methods of the appended claims are not limited in scope by the specific apparatus and methods described herein, which are intended as illustrations of a few aspects of the claims and any apparatus and methods that are functionally equivalent are intended to fall within the scope of the claims. Various modifications of the apparatus and methods in addition to those shown and described herein are intended to fall within the scope of the appended claims. Further, while only certain representative components and method steps disclosed herein are specifically described, other combinations of the components and method steps also are intended to fall within the scope of the appended claims, even if not specifically recited. Thus, a combination of steps, elements, or components may be explicitly mentioned herein; however, other combinations of steps, elements, and components are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The invention claimed is:

1. An apparatus for determining conditions of hemorrhage in a subject, comprising:
at least an input line for:
receiving one or more electrical signals coming from one or more electrodes predisposed to detect cardiac activity; and
receiving a signal coming from a peripheral sensor predisposed to operate in a predetermined peripheral section of the subject's body;
a control unit connected to the input line and configured for:
determining, from the one or more electrical signals coming from the one or more electrodes through the input line, an instant of generation ($TG_j$) in which a pressoric wave is generated in relation to a heartbeat, determining, from the signal coming from the peripheral sensor through the input line, an instant of peripheral propagation ($TP_j$) in which the pressoric wave reaches the predetermined peripheral section, calculating at least one value of an indicator parameter (iHAT) as a function of a temporal delay ($\delta T_j$) occurring between the instant of generation ($TG_j$) and the instant of peripheral propagation ($TP_j$) divided by the temporal interval occurring between two successive heartbeats ($\Delta T_j$), verifying whether or not said at least one value of the indicator parameter (iHAT) satisfies a reference criterion, and determining whether a condition of hemorrhage is present or not in the subject depending upon an outcome of said verifying.

2. The apparatus of claim 1, wherein the control unit is configured for:

determining a temporal interval ($\Delta T_j$) between a heartbeat and a following heartbeat, and calculating the value of the indicator parameter (iHAT) as a function of at least:
the instant of generation ($TG_j$),
the instant of peripheral propagation ($TP_j$), and
the temporal interval ($66\ T_j$).

3. The apparatus of claim 1, wherein the control unit is configured for:

determining an ECG chart from the one or more electric signals coming from the one or more electrodes; and identifying the instant of generation ($TG_j$) as a moment in which, in the ECG chart, a wave ($R_j$) relating to a sequence of waves $(QRS)_j$ exhibits a maximum peak.

4. The apparatus of claim 1, wherein the peripheral sensor comprises a pulse oximeter and wherein the control unit is configured for:

determining a saturometer curve from a signal coming from the pulse oximeter, and identifying the instant of peripheral propagation ($TP_j$) by detecting a peak in amplitude of the saturometer curve.

5. The apparatus of claim 4, wherein the control unit is configured such as to temporally synchronise the ECG chart and the saturometer curve by relating values of the ECG chart and the saturometer curve to a same temporal axis.

6. The apparatus of claim 1, wherein verifying comprises at least one of the following verification steps:

verifying if an instant value of the indicator parameter (iHAT) is higher than a prefixed threshold value;

verifying if a mean value of the indicator parameter (iHAT) is higher than the prefixed threshold value, the mean value of the indicator parameter being calculated as a mean of a plurality of instant values of the indicator parameter (iHAT) related to a plurality of successive heartbeats;

verifying if a gradient of instant values of the indicator parameter (iHAT) changes across time beyond a prefixed threshold gradient;

verifying if a gradient of mean values ($iHAT_{med}$) of the indicator parameter (iHAT) changes across time beyond the prefixed threshold gradient, each mean value of the indicator parameter being calculated as a mean of a plurality of instant values of the indicator parameter (iHAT) related to a plurality of successive heartbeats;

verifying if a distribution of the instant values of the indicator parameter (iHAT) around their mean value changes across time beyond a prefixed distribution level;

and wherein determining whether a condition of hemorrhage is present or not comprises determining if one or more of the above verification steps is positively passed and in an affirmative concluding that hemorrhage exists in the subject.

7. The apparatus of claim 6, wherein the control unit is configured such as to represent, in a first graphic mode, the instant value and/or the mean value of the indicator parameter when lower than the prefixed threshold, and in a second graphic mode, different to the first graphic mode, the instant value and/or the mean value of the indicator parameter (iHAT; iHATmed) when higher than the prefixed threshold.

8. The apparatus of claim 6, wherein the control unit is configured to compare at least one of the instant value of the indicator parameter and the mean value of the indicator parameter (THAT; iHATmed) with a plurality of respective threshold values defining a series of potentially dangerous intervals, the control unit being further configured to generate a respective control signal when each of the respective threshold values has been exceeded and to send each said respective control signal to an output device to inform an operator in a graphically and/or acoustic different way when the subject reaches different levels of hemorrhage.

9. The apparatus of claim 6, wherein the prefixed threshold value to which the instant or the mean value of the indicator parameter (iHAT) is one of:
a predefined value comprised between 55% and 60%,
a predefined value substantially equal to 58%, or
a calculated value the control unit is configured to enable programming of.

10. The apparatus of claim 1, wherein the control unit is further configured to calculate the amount of hemorrhage, optionally as blood volume fraction relative to the subject's total blood volume, as a function of a detected value of the indicator parameter (iHAT), optionally wherein said amount of hemorrhage is calculated as a linear function of the detected value of the indicator parameter (iHAT).

11. The apparatus of claim 1, comprising at least a first input line for receiving the one or more electrical signals coming from the electrodes; at least a second input line, distinct from the first input line, for receiving the signal coming from the peripheral sensor.

12. The apparatus of claim 1, wherein the control unit is configured to:

repeat a calculation of the value of the indicator parameter a plurality of times, in relation to a plurality of successive heartbeats; and determine a mean value ($iHAT_{med}$) of the indicator parameter, the mean value being calculated as a mean of a plurality of parameter values (iHAT) related to the plurality of successive heartbeats.

13. The apparatus of claim 1, wherein it comprises an output device selected from the group of a viewing device and an acoustic device, the control unit being connected to the output device and being configured to:

generate a control signal when a condition of hemorrhage in a patient has been determined, and send the control signal the output device in order to provide at least one of an acoustic and a visual indication to an operator to indicate that the subject reached a condition of hemorrhage.

14. The apparatus of claim 13, wherein the control unit is configured to:

form, on the viewing device, a plurality of viewing fields which are distinct from one another, display on a field of the viewing fields a temporally-synchronised graphic representation of the ECG chart and a pulse oximeter signal; and display, on the viewing field of the viewing device, a graphic representation of a temporal progression of the value of the indicator parameter and/or of the mean value of the indicator parameter value (iHAT; $iHAT_{med}$).

15. The apparatus of claim 14, wherein the control unit is configured to represent fiduciary markers in a differentiated way, which fiduciary markers respectively relate to peaks ($R_j$) of a wave (R) in the ECG chart and to peaks ($S_j$) in the saturometer curve.

16. An apparatus for determining a blood hemorrhage volume lost in a subject, comprising:
    at least an input line for:
        receiving one or more electrical signals coming from one or more electrodes predisposed to detect cardiac activity;
        receiving a signal coming from a peripheral sensor predisposed to operate in a predetermined peripheral section of the subject's body;
    a control unit connected to the input line and configured for:
        determining, from the one or more signals coming from the one or more electrodes through the input line, an instant of generation ($TG_j$) in which a pressoric wave is generated in relation to a heartbeat,
        determining, from the signal coming from the peripheral sensor through the input line, an instant of peripheral propagation ($TP_j$) in which the pressoric wave reaches the predetermined peripheral section,
        calculating at least one value of an indicator parameter (iHAT) as a function of at least the instant of generation ($TG_j$) and the instant of peripheral propagation ($TP_j$), and
        calculating an amount of hemorrhage volume as a function of a detected value of the indicator parameter (iHAT).

17. The apparatus of claim 16, wherein the hemorrhage volume is calculated as blood volume fraction relative to the subject's total blood volume.

18. The apparatus of claim 16, wherein said amount of hemorrhage volume is calculated as a linear function of the detected value of the indicator parameter (iHAT).

19. The apparatus of claim 16, wherein the control unit is configured for:
    determining a temporal interval ($\Delta T_j$) between a heartbeat and a following heartbeat, and a temporal delay ($\delta T_j$) occurring between the instant of generation ($TG_j$) and the instant of peripheral propagation ($TP_j$) and
    calculating the value of the indicator parameter (iHAT) as a function of at least the temporal interval ($\Delta T_j$) and the temporal delay ($\delta T_j$).

20. The apparatus of claim 16, wherein the peripheral sensor comprises a pulse oximeter and wherein the control unit is configured for:
    determining a saturometer curve from a signal coming from the pulse oximeter, and
    identifying the instant of peripheral propagation ($TP_j$) by detecting a peak in amplitude of the saturometer curve.

21. The apparatus of claim 16, wherein the control unit is configured to execute a verifying step wherein the verifying step comprises at least one of the following verification steps:
    verifying if an instant value of the indicator parameter (iHAT) is higher than a prefixed threshold value;
    verifying if a mean value of the indicator parameter (iHAT) is higher than the prefixed threshold value, the mean value of the indicator parameter being calculated as a mean of a plurality of instant values of the indicator parameter (iHAT) related to a plurality of successive heartbeats;
    verifying if a gradient of instant values of the indicator parameter (iHAT) changes across time beyond a prefixed threshold gradient;
    verifying if a gradient of mean values ($iHAT_{med}$) of the indicator parameter (iHAT) changes across time beyond the prefixed threshold gradient, each mean value of the indicator parameter being calculated as a mean of a plurality of instant values of the indicator parameter (iHAT) related to a plurality of successive heartbeats; and
    verifying if a distribution of the instant values of the indicator parameter (iHAT) around their mean value changes across time beyond a prefixed distribution level; and
    wherein determining whether a condition of hemorrhage is present or not comprises determining if one or more of the above verification steps is positively passed and in an affirmative concluding that hemorrhage exists in the subject.

22. An apparatus for determining an amount of hemorrhage in a subject, comprising:
    at least an input line for:
        receiving one or more electrical signals coming from one or more electrodes predisposed to detect cardiac activity; and
        receiving a signal coming from a peripheral sensor predisposed to operate in a predetermined peripheral section of the subject's body;
    a control unit connected to the input line and configured for:
        determining, from the one or more electrical signals coming from the one or more electrodes through the input line, an instant of generation ($TG_j$) in which a pressoric wave is generated in relation to a heartbeat,
        determining, from the signal coming from the peripheral sensor through the input line, an instant of peripheral propagation ($TP_j$) in which the pressoric wave reaches the predetermined peripheral section,
        calculating at least one value of an indicator parameter (iHAT) as a function of at least the instant of generation ($TG_j$) and the instant of peripheral propagation ($TP_j$),
        calculating the amount of hemorrhage as a function of the a detected value of the indicator parameter (iHAT).

23. Apparatus according to claim 22, wherein the control unit is configured for calculating the amount of hemorrhage as blood volume fraction relative to the subject's total blood volume.

24. Apparatus according to claim 22, wherein the control unit is configured for calculating the amount of hemorrhage as a linear function of the detected value of the indicator parameter (iHAT).

25. The apparatus of claim 22, wherein the control unit is configured for:
    determining a temporal interval ($\Delta Tj$) between a heartbeat and a following heartbeat, and a temporal delay ($\delta Tj$) occurring between the instant of generation (TGj) and the instant of peripheral propagation (TPj) and
    calculating the value of the indicator value parameter value (iHAT) as a function of at least the temporal interval ($\Delta Tj$) and the temporal delay ($\delta Tj$).

* * * * *

UNITED STATES PATENT AND TRADEMARK OFFICE
CERTIFICATE OF CORRECTION

PATENT NO. : 8,517,950 B2
APPLICATION NO. : 13/222692
DATED : August 27, 2013
INVENTOR(S) : Marco Vettorello It is certified that error appears in the above-identified patent and that said Letters Patent is hereby corrected as shown below:

In the Claims

In claim 2, in column 21, line 25, please delete "temporal interval (66 Tj)" and insert therefor -- temporal interval ($\Delta Tj$) --.

Signed and Sealed this
Tenth Day of December, 2013

Margaret A. Focarino
*Commissioner for Patents of the United States Patent and Trademark Office*